(12) United States Patent
Di (10) Patent No.: US 10,947,558 B2
(45) Date of Patent: Mar. 16, 2021

(54) COMPOSITIONS AND METHODS FOR INDUCING RESISTANCE TO SOYBEAN CYST NEMATODE VIA RNAI

(71) Applicant: Rutgers, The State University of New Jersey, New Brunswick, NJ (US)

(72) Inventor: Rong Di, East Brunswick, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 254 days.

(21) Appl. No.: 15/746,718

(22) PCT Filed: Jul. 22, 2016

(86) PCT No.: PCT/US2016/043706
§ 371 (c)(1),
(2) Date: Jan. 22, 2018

(87) PCT Pub. No.: WO2017/015621
PCT Pub. Date: Jan. 26, 2017

(65) Prior Publication Data
US 2019/0106707 A1 Apr. 11, 2019

Related U.S. Application Data

(60) Provisional application No. 62/195,482, filed on Jul. 22, 2015.

(51) Int. Cl.
*C12N 15/82* (2006.01)
*C12N 15/113* (2010.01)

(52) U.S. Cl.
CPC ........ *C12N 15/8286* (2013.01); *C12N 15/113* (2013.01); *C12N 15/8201* (2013.01); *C12N 15/8218* (2013.01); *C12N 2310/14* (2013.01); *Y02A 40/146* (2018.01)

(58) Field of Classification Search
None
See application file for complete search history.

(56) References Cited

U.S. PATENT DOCUMENTS

| | | | | |
|---|---|---|---|---|
| 2003/0177536 A1* | 9/2003 | Grundler | ............. | C07K 14/415 800/288 |
| 2014/0007296 A1* | 1/2014 | Huang | ................ | C12N 15/113 800/279 |

OTHER PUBLICATIONS

Bekai, Sadia et al., "A SNARE-Like Protein and Biotin Are Implicated in Soybean Cyst Nematode Virulence", PLoS ONE, 10(12): e0145601. doi:10.1371/journal.pone.0145601 (2015).
Guo, Xiaoli et al., "Enhanced resistance to soybean cyst nematode Heterodera glycines in transgenic soybean by silencing putative CLE receptors", Plant Biotechnology Journal, 13: 801-810 (2015).
Hamamouch, Noureddine et al., The interaction of the novel 30C02 cyst nematode effector protein with a plant B-1,3-endoglucanase may suppress host defence to promote parasitism, Journal of Experimental Botany, 63(10): 3683-3696 (2012).
Jinke, Martin et al., "A programmable dual RNA-guided DNA endonuclease in adaptive bacterial immunity", Science, 17: 337(6096): 816-8212 (2012).
Kulcheski, Franceli R. et al.. "Identification of novel soybean microRNAs involved in abiotic and biotic stresses", BMC Genomics, 12: 307 (2011).
Lin, Jingyu et al., "Transgenic soybean overexpressing GmSAMT1 exhibits resistance to multiple-HG types of soybean cyst nematode Hegterodera glycines", Plant Biotechnology Journal, 14: 2100-2109 (2016).
Lin, Jingyu et al., "Overexpression of a soybean salicylic acid methyltransferase gene confers resistance to soybean cyst nematode", Plant Biotechnology Journal, 11: 1135-1145 (2013).
Matthews, Benjamin F. et al., "*Arabidopsis* genes, AtNPR1, AtTGA2 and AtPR-5, confer partial resistance to soybean cyst nematode (Heterodera glycines) when overexpressed in transgenic soybean roots", BMC Plant Biology, 14: 96 (2014).
Peng, Huan et al., "Novel Pectate Lyase Genes of Heterodera glycines Play Key Roles in the Early Stage of Parasitism", PLoS ONE, 1(3): e0149959. doi:10.1371/journal.pone.0149959 (2016).
Riggs, R.D. et al., "Optimization of the Heterodera glycines Race Test Procedure", Journal of Nematology, 23(2): 149-154 (1991).
Steeves, Ryan M. et al., "Transgenic soybeans expressing siRNAs specific to a major sperm protein gene suppress Heterodera glycines reproduction", Functional Plant Biology, 33: 991-999 (2006).
Wang, Yanpeng et al., "Simultaneous editing of three homoeoalleles in hexaploid bread wheat confers heritable resistance to powdery mildew", Nature Biotechnology, 32(9): 947-951 (2014).
Xie, Kabin et al., "RNA-Guided Genome Editing in Plants Using a CRISPR-Cas System", Molecular Plant, 6(6): 1975-1983 (2013).
Yang, Heping et al., "A novel real-time polymerase chain reaction method for high throughput quantification of small regulatory RNAs", Plant Biotechnology Journal, 7: 621-630 (2009).
Zhou, Lian et al., "Overexpression of GmAKT2 potassium channel enhances resistance to soybean mosaic virus", BMC Plant Biology, 14: 154 (2014).

* cited by examiner

*Primary Examiner* — Stephen Uyeno
(74) *Attorney, Agent, or Firm* — Kathleen D. Rigaut; Howson & Howson LLP (57) ABSTRACT

RNAi compositions and methods are provided which inhibit soybean nematode cyst infestation. Also disclosed are plants comprising said RNAi.

6 Claims, 5 Drawing Sheets

Specification includes a Sequence Listing.

Fig. 1A                          Fig. 1B

```
  1 caaaatcaca cgtgaccagc tgaacgagag tgtggctgaa atcttgaaac aatcccaaga
 61 gaagaagcgc aatttccgag aaacgattga attgcaaatt gctctgaaaa actacgaccc
121 acagaaggac aagcgtttca gtggaactgt tagactgaag cacatccctc gtccgaaaac
181 gaaggtttgc atccttggcg accaaaaaca ttgtgacgag gccaatgcca acggaattcc
241 atgcatgaca gcggacgacc tgaagaagtt gaacaaggac aagaagctga tctaaaagct
301 cagcaaaagc taccacgctt ccttgccttt cgaatcactc atcaaacaaa tccctcgtat
361 tcttggtccc ggactgaaca aggctggcaa gttcccaagt gtggtgtcac acaacgacat
421 gctgaacgca aaggtggatg aagtgaaggc gaaccgcaaa ttcgaaatga aacaggtgct
481 c
```

Fig. 2B aagctttgtaccaacaacttgactaggattctaagttctttttatgtataggatgtctatattaaactaccatgactaacatatata
tagtagttccatatgctcgataaactatgatagatcaacaattttaaacatatagtttaacactatttatttgttcaacg
tcaatagtttatagttcgcatgcgctcggcttagatttggtccccaacagtcgaaattgtcaaataatataaaataaaag
tttcattgttaggattcatttattcttcgggtggttattgtaataaaaggcaaaagaaaaagaagaacaaaattcacaag
taaaaaaaagataacatcattcttttagtcgacaaaaaaaaaaaaaaatcaaaaagatttattcagtactacagttta
atattgttttgacttttttcttttttcttttatattatctgaaaattctagactgcagctgaaacatgtgatatggattaaa
ggcgtatccagtatccacagaaagaggagtggtgtcgctcacccagtcacccttgttacttgttagatagcattaataca
tttgtaagcaacagcttatctaatagacatgtcttaattgggaaatatgctctaagatgatacaaccatggttccaactg
ttgaccaccataactgataacatgttgattacatttttcttttcagttacaacgattacttttttggggaaattattga
tataatatgattcattggatgatccgatatcatgcatataaagttgtatctcgtgaaacacgagatagtattatactcca
ttctttcattatcggagtatgtttaaaatttgaaaacaaatacagacacggaccgtggtctttaccttcagaaaaaaaaa
gagaaaaaaaacaatccactgtttattataggagttgtagaaaatcgggcaacgatattcgatatgagttattattagg
gccttattattatatggtattactggatattactaaataatcatataaatatcacattttaatatacactcgttggacac
gcggaatattatatgttctaaatgttaaaaaatcaacagaatacaacgatcgacggatctagagtctagaccatgcaaat
acctcatcctatttacatataataactgtgcatatagtttagtcaaataaaaaggtaaagaaacaatatacaacctataa
cgtcaatatccatgtacgtagtaataattaggatatgacacgaacacacgatatcttgatatatacaaaatgaaaactta
aaaattgattaatatggcctggctgggtatattattaaaaaaacataaagagagatcaataattgattcgaagatcacta
tataaagaacgtcttcgatatgtaaaagaaccatcctaaacatttttcttgaataaaatcagaattacaaacaaaa
ggatccacgatgcgcaatttccgagaaacgattgaattgcaaattgctctgaaaaactacgacccacagaaggacaagcg
tttcagtggaactgttagactgaagcacatccctcgtccgaaaacgaaggtttgcatccttggcgaccaaaaacattgtg
acgaggccaatgccaacggaattccatgcatgacagcggacgacctgaagaagttgaacaaggacaagaagctgatctaa
tcttttttcctttttagtataaaatagttaagtgatgttaattagtatgattataataatatagttgttataattgtgaaa
aaataatttataaatatattgtttacataaacaacatagtaatgtaaaaaaatatgacaagtgatgtgtaagacgaagaa
gataaaagttgagagtaagtatattattttttaatgaatttgatcgaacatgtaagatgatatactagcattaatatttgt
tttaatcataatagtaattctagctggtttgatgaattaaatatcaatgataaaatactatagtaaaaataagaataaat
aaattaaaataatatttttttatgattaatagtttattatataattaaatatctataccattactaaatattttagttta
aaagttaataaatattttgttagaaattccaatctgcttgtaatttatcaataaacaaaatattaaataacaagctaaag
taacaaataatatcaaactaatagaaacagtaatctaatgtaacaaaacataatctaatgctaatataacaaagcgcaag
atctatcatttatatagtattattttcaatcaacattcttattaatttctaaataatacttgtagttttattaacttct
aaatggattgactattaattaaatgaattagtcgaacatgaataaacaaggtaacatgatagatcatgtcattgtgttat
cattgatcttacatttggattgttagatcagcttcttgtccttgttcaacttcttcaggtcgtccgctgtcatgcatggaattccgttggcattggcctcgtcacaatgttttt
ggtcgccaaggatgcaaaccttcgttttcggacgagggatgtgcttcagtctaacagttccactgaaa
cgcttgtccttctgtgggtcgtagttttcagagcaatttgcaattcaatcgtttctcggaaattgcgcat
ctgctttaatgagatatgcgagacgcctatgatcgcatgatatttgctttcaattctgttgtgcacgttgtaaaaaacct
gagcatgtgtagctcagatccttaccgccggtttcggttcattctaatgaatatatcacccgttactatcgtattttat
gaataatattctccgttcaatttactgattgtaccctactacttatatgtacaatattaaaatgaaaacaatatattgtg
ctgaataggtttatagcgacatctatgatagagcgccacaataacaaacaattgcgttttattattacaaatccaatttt
aaaaaaagcggcagaaccggtcaaacctaaaagactgattacataaatcttattcaaatttcaaaaggccccaggggcta
gtatctacgacacaccgagcggcgaactaataacgttcactgaagggaactccggttccccgccggcgcgcatgggtgag
attccttgaagttgagtattggccgtccgctctaccgaaagttacgggcaccattcaacccggtccagcacggcggccgg
gtaaccgacttgctgccccgagaattatgcagcatttttttggtgtatgtgggccccaaatgaagtgcaggtcaaaccctt
gacagtgacgacaaatcgtttgggcgggtccagggcgaattttgcgacaacatgtcgaggctcagcaggacctgcaggcat
gcaagctagcttactagtgatgcatattctatagtgtcacctaaatgagctc

COMPOSITIONS AND METHODS FOR INDUCING RESISTANCE TO SOYBEAN CYST NEMATODE VIA R preferred embodiment, the construct is contained within an expression vector, pRD64 (SEQ ID NO: 2).

Finally, the invention also provides soybean plant comprising the RNAi construct described above and nematode resistant progeny thereof

BRIEF DESCRIPTION OF THE DRAWINGS

FIGS. 1A-1C show micrographs of *Heterodera glycines* (FIGS. 1A and 1B) and the sequence of HgRPS23 (FIG. 1C; (SEQ ID NO: 1). Adult females and cysts of SCN are about ⅟₃₂ of an inch and appear long and visible to the unaided eye. The SCN life cycle is between 24-30 days and is divided into three phases, egg, juvenile and adult. One female SCN can produce 200-400 eggs in its tough sac. The pest is spread primarily through soil.

FIG.

reproduce, or to limit nematode-related damage or loss in crop plants. To "control" nematodes may or may not mean killing the nematodes.

A "nematode-controlling effective amount" as used herein refers to the concentration of an RNAi capable of inhibiting, through a toxic effect, the ability of nematodes to survive, grow, feed and/or reproduce, or of reducing or preventing nematode-related damage or loss in crop plants. "Nematode-controlling effective amount" may or may not mean killing the nematodes.

"Expression cassette" as used herein means a nucleic acid sequence capable of directing expression of a particular nucleotide sequence in an appropriate host cell, comprising a promoter operably linked to the nucleotide sequence of interest which is operably linked to termination signals. It also typically comprises sequences required for proper translation of the nucleotide sequence. The expression cassette comprising the nucleotide sequence of interest may be chimeric, meaning that at least one of its components is heterologous with respect to at least one of its other components. The expression cassette may also be one that is naturally occurring but has been obtained in a recombinant form useful for heterologous expression. Typically, however, the expression cassette is heterologous with respect to the host, i.e., the particular nucleic acid sequence of the expression cassette does not occur naturally in the host cell and must have been introduced into the host cell or an ancestor of the host cell by a transformation event. The expression of the nucleotide sequence in the expression cassette may be under the control of a constitutive promoter or of an inducible promoter that initiates transcription only when the host cell is exposed to some particular external stimulus. In the case of a multicellular organism, such as a plant, the promoter can also be specific to a particular tissue, or organ, or stage of development.

A "gene" is a defined region that is located within a genome and that, besides the aforementioned coding nucleic acid sequence, comprises other, primarily regulatory, nucleic acid sequences responsible for the control of the expression, that is to say the transcription and translation, of the coding portion. A gene may also comprise other 5' and 3' untranslated sequences and termination sequences. Further elements that may be present are, for example, introns.

A "heterologous" nucleic acid sequence is a nucleic acid sequence not naturally associated with a host cell into which it is introduced, including non-naturally occurring multiple copies of a naturally occurring nucleic acid sequence.

"Nematicidal" is defined as a toxic biological activity capable of controlling nematodes, preferably by killing them.

A "plant" is any plant at any stage of development, particularly a seed plant.

A "plant cell" is a structural and physiological unit of a plant, comprising a protoplast and a cell wall. The plant cell may be in the form of an isolated single cell or a cultured cell, or as a part of higher organized unit such as, for example, plant tissue, a plant organ, or a whole plant.

"Plant material" refers to leaves, stems, roots, flowers or flower parts, fruits, pollen, egg cells, zygotes, seeds, cuttings, cell or tissue cultures, or any other part or product of a plant.

A "plant organ" is a distinct and visibly structured and differentiated part of a plant such as a root, stem, leaf, flower bud, or embryo.

A "plant part" may be any part of a plant and include a plant cell, plant material, plant organ or plant tissue.

"Plant tissue" as used herein means a group of plant cells organized into a structural and functional unit. Any tissue of a plant in planta or in culture is included. This term includes, but is not limited to, whole plants, plant organs, plant seeds, tissue culture and any groups of plant cells organized into structural and/or functional units. The use of this term in conjunction with, or in the absence of, any specific type of plant tissue as listed above or otherwise embraced by this definition is not intended to be exclusive of any other type of plant tissue.

A "promoter" is an untranslated DNA sequence upstream of the coding region that contains the binding site for RNA polymerase II and initiates transcription of the DNA. The promoter region may also include other elements that act as regulators of gene expression.

"Regulatory elements" refer to sequences involved in controlling the expression of a nucleotide sequence. Regulatory elements comprise a promoter operably linked to the nucleotide sequence of interest and termination signals. They also typically encompass sequences required for proper translation of the nucleotide sequence.

Many techniques are available to those skilled in the art to facilitate transformation, transfection, or transduction of the expression construct into a prokaryotic or eukaryotic organism. The terms "transformation", "transfection", and "transduction" refer to methods of inserting a nucleic acid and/or expression construct into a cell or host organism. These methods involve a variety of techniques, such as treating the cells with high concentrations of salt, an electric field, or detergent, to render the host cell outer membrane or wall permeable to nucleic acid molecules of interest, microinjection, peptide-tethering, PEG-fusion, and the like. Transformation of soybean can be can also be accomplished using *Agrobacterium* mediated transduction and biolistic delivery of RNAi coated microparticles.

The materials and methods set forth below are provided to facilitate the practice of the present invention.

Construction of HgRPS23 RNAi Transformation Vector

The reported 362 bp of HgRPS23 gene (GenBank accession No. BF014259; SEQ ID NO: 1) (Alkharouf et al., 2007) was compared to the *C. elegans* CeRPL1 (Y71F9AL.13, GenBank accession No. NM_058660). The most conserved 225 bp within the 362 bp of HgRPS23 was selected to make the hairpin construct for soybean RNAi vector. In order to express the siRNA only in soybean roots, the root-specific promoter of *Arabidopsis* pyk10 gene (Li et al., 2009; Nitz et al., 2001) was chosen to drive the expression of the HgRPS23 hairpin structure. The intron to separate the HgRPS23 inverted repeats was from the pyruvate orthophosphate dikinase as in the pHANNIBAL vector (GenBank accession No. AJ311872). The terminator was from the octopine synthase as in pBI121 vector (GenBank accession No. AJ485783). The complete HgRPS23 cassette was synthesized by GenScript (Piscataway, N.J.), and digested by HindIII and SacI and then sub-cloned into the soybean expression vector pTF101.1 supplied by the Plant Transformation Facility, Iowa State University (Paz et al., 2006), resulting in pRD64 (SEQ ID NO: 2). Any RNAi between 18-23 nucleotides in length that hybridizes to SEQ ID NO: 1 which is effective to silence HgRPS23 may be used in the methods and constructs of the current invention.

Evaluation of HgRPS23 RNAi in *C. elegans*

The effectiveness of HgRPS23 siRNA in silencing the worm's ribosomal protein gene was tested in *C. elegans*, following the previously published protocols (Alkharouf et al., 2007, Peng et al., 2016) with modifications. A T7 promoter sequence (5'-TAATACGACTCACTATAG-3';

SEQ ID NO: 3) was added to the 5' ends of both the forward and reverse primer to amplify the 225 bp of HgRPS23 from pRD64 by PCR. The amplified PCR product was used to produce the double stranded (ds) in vitro transcript by the MEGAscript®T7 kit (Ambion/Invitrogen, Calsbad, Calif., USA).

The wt N2 strain of *C. elegans* was obtained from the CGC (*Caenorhabditis* Genetics Center) and maintained on NGM (Nematode Growth Medium) plates (60 mm petri dishes) at room temperature. The worms were grown and synchronized using protocols from the WormBase (www.wormbase.org). The L2 worms were soaked in 100 μl M9 buffer (22 mM $KH_2PO_4$, 4.7 mM $NH_4Cl$, 43.6 mM $Na_2HPO_4$ and 2.1 mM NaCl) containing 50 mM octopamine (Sigma, St. Louis, Mo., USA) to increase pharyngeal pumping and 2 mg/ml HgRPS23 dsRNA. The negative control L2 worms were treated by soaking in M9 buffer containing 50 mM octopamine only. The positive control L2 worms were soaked in M9 buffer containing 50 mM octopamine and 10 μM cycloheximide (Sigma, St. Louis, Mo., USA) as a translation inhibitor. *C. elegans* worms were treated in the wells of a 96-well plate on a gentle shaker. The vitality of worms was observed under a stereo microscope. Treated worms were then collected by centrifugation at 300 g for 2 min and stained with M9 buffer containing 1 μM SYTOX Green nucleic acid stain (Invitrogen, Calsbad, Calif., USA). The stained dead worms were distinguished from the non-stained live worms by observation under the Olympus SZX16 stereomicroscope (Olympus, Tokyo, Japan).

Production of Transgenic Soybean Plants Expressing SCN-Specific siRNAs

The HgRPS23 siRNA vector pRD64 was provided to the Plant Transformation Facility, Iowa State University and was transformed into *Agrobacterium tumefaciens* strain EHA101 for soybean transformation (Paz et al., 2000. Briefly, half-seed explants were excised from disinfected soybean (cv. Williams 82) mature seeds that had been soaked in sterile water overnight. The explants were incubated with *A. tumefaciens* containing pRD64 for 30 min and then co-cultivated for 5 days. Explants were incubated on shoot induction medium I containing B5 medium and vitamins, 30 g/l sucrose, 1.11 mg/l BAP and the antibiotic regime of 50 mg/l timentin, 200 mg/l cefotaxime and 50 mg/l vancomycin for 14 days. The explants were subsequently transferred to the shoot induction medium I supplemented with 6 mg/l glufosinate for 14 days under 18:6 photoperiod. After another 14 days on shoot induction medium I with 6 mg/l glufosinate, the explants were transferred to shoot elongation medium containing MS salts and B5 vitamins supplemented with MSIII iron stock, 30 g/l sucrose, 0.1 mg/l IAA, 0.5 mg/l $GA_3$, 1 mg/l zeatin riboside, the antibiotic regime as above and 6 mg/l glufosinate to select transgenic shoots. Individual shoot was dipped in 1 mg/l IBA and transferred to rooting medium containing MS salts and B5 vitamins, MSIII iron stock and 20 g/l sucrose, without the glufosinate. Rooted plantlets were transferred to soil and acclimatized to greenhouse conditions. $T_1$ transgenic soybean seeds were shipped back to Rutgers University with the USDA-APHIS transgenic plant movement permit. Notably, particle gun bombardment can also be used to introduce the siRNAi vector of the invention into recipient soybean plants.

Regenerated $T_0$, $T_1$ and $T_2$ transgenic soybean plants at two trifoliate leaf stage were tested by the herbicide paint assay to confirm their expression of the bar gene (Paz et al. 2006). The FINALE herbicide was diluted with water to contain 150 mg/l of the active ingredient of glufosinate ammonium. A Q-tip was used to evenly paint the diluted herbicide over the trifoliate leaves. Plants were observed visually every day for the symptoms of yellowing and necrosis on the leaves.

Figure 5:
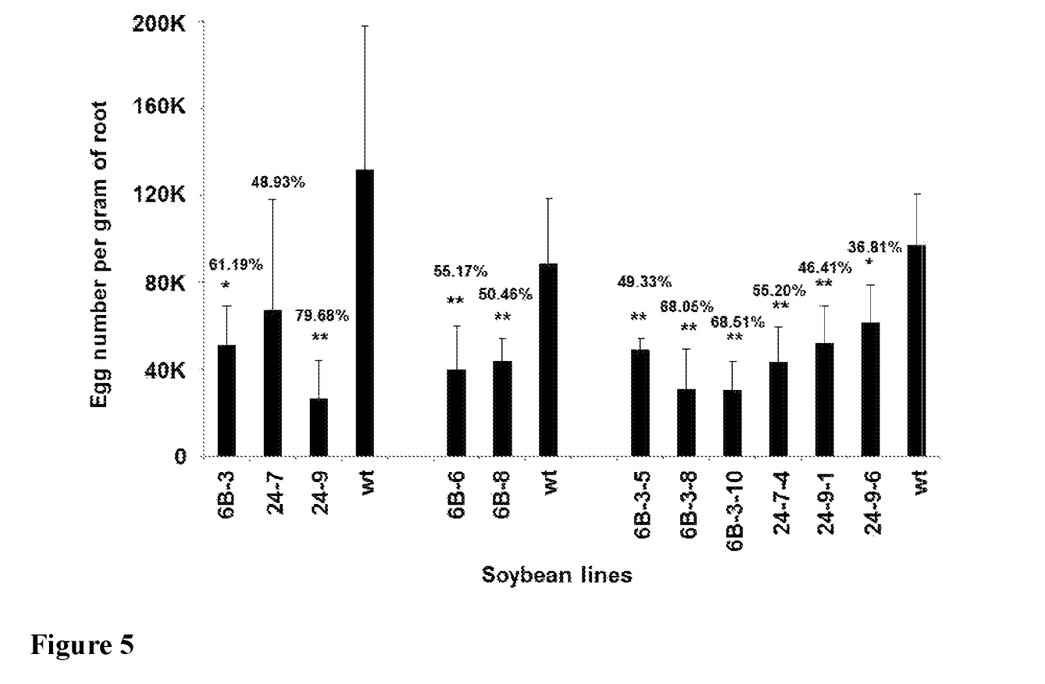

Analysis of HgRPS23 siRNA Expression Level in Transgenic Soybean by TaqMan-Based RT-qPCR The siRNA species that could be potentially produced from the HgRPS23 225-bp RNAi repeat in transgenic soybean plants were predicted by the online program SIRNA from EMBOSS (http://bioweb.pasteur.fr/seqanal/interfaces/sirna.html#outseq) (Yang et al., 2009). siRNA species (5' AAACUACGACCCACAGAAGGA 3'; (SEQ ID NO: 4) had the top score of 9.0. The expression level of this HgRPS23 siRNA in pRD64-transgenic soybean plants was evaluated by RT-qPCR using the uniquely designed key-like RT primer and TaqMan probe (Yang et al., 2009) (FIG. 5). The 5× key-like primer and 20× TaqMan assay containing the forward and reverse primers and the TaqMan probe for the predicted HgRPS23 siRNA species were synthesized by Applied Biosystems (Thermo Fisher, Waltham, Mass., USA). Total RNA was isolated from each soybean plant using the TRIzol® reagent (Invitrogen, Calsbad, Calif., USA) following the manufacturer's instructions. The RNA concentration was measured by a Nanodrop spectrophotomer (Thermo Fisher, Waltham, Mass., USA). Using 100 ng RNA per sample, 1× key-like primer, the reverse transcription reaction was conducted with the High Capacity cDNA Synthesis Kit (Applied Biosystems, Thermo Fisher, Waltham, Mass., USA) in a 10 μl reaction. After 1:1 dilution of the cDNA with sterile water, qPCR reaction was performed with 1 μl of the diluted cDNA, 1× TaqMan assay, and 1× TaqMan master mix (Applied Biosystems, Thermo Fisher, Waltham, Mass., USA) in a 10 μl reaction with the StepOnePlus thermocycler (Applied Biosystems, Thermo Fisher, Waltham, Mass., USA). The cycling condition was as follows: 50° C., 2 min, 1 cycle; 95° C., 10 min, 1 cycle; 95° C., 15 sec, 60° C., 1 min, 40 cycles. The $2^{-\Delta\Delta ct}$ relative quantification method was used to analyze the siRNA (5' AAACUACGACCCACAGAAGGA 3'; SEQ ID NO: 4) level, in the roots with soybean MIR156b (5' UGACAGAAGAGAGAGAGCACA 3'; (SEQ ID NO: 5) (Kulcheski et al., 2011) as the reference, and in the leaves with MIR159 (5' UUUGGAUUGAAGGGAGCUCUA 3'; (SEQ ID NO: 6) as the reference (Itaya et al., 2008).

Analysis of Transgenic Soybean for SCN Resistance

The $T_1$ and $T_2$ transgenic soybean plants were inoculated with *H. glycines* OP50 eggs as described (Hamamouch et al., 2012) to test their resistance to SCN. Briefly, *H. glycines* OP50 was maintained on soybean plants. Cysts were collected by 850 μm and then 250 μm sieving from infected soybean roots after 2-3 months of infection. SCN eggs were isolated from the cysts by 70% sucrose solution separation and 25 μm sieving and quantitated. Transgenic and wt soybean (Williams 82) seeds were sowed in 150 ml plastic cone containers and plants were maintained in a greenhouse. After seeds were germinated for 2 weeks, 5000 SCN eggs were inoculated into each cone containing a single plant. Fifty days post inoculation, plant height was measured, roots were separated from plants and weighed. The SCN cysts and eggs were collected and counted.

The following example is provided to illustrate certain embodiments of the invention. It is not intended to limit the invention in any way.

Example I

Construction of HgRPS23 RNAi Plant Transformation Vector

As shown by Alkharouf et al. (Alkharouf et al. 2007), RNA interference (RNAi) with dsRNA (double-stranded RNA) produced from a 362 bp-fragment of the SCN ribosomal HgRPS23 gene (Accession No. BF014259) led to lethality of SCN J2 nematodes. Our bioinformatics analysis showed that the N-terminal 75 amino acid sequence from this 362-bp fragment of HgRPS23 shares 73.3% homology with the C. elegans N-terminus of the ribosomal protein large subunit (WP:CE25552 Y71F9AL.13, CeRPL1, Accession No. NM_058660), confirming the author's claim in GenBank. The nucleotide sequences between HgRPS23 and CeRPL1 also share 76.4% homology. We selected the most conserved 225 bp within the HgRPS23 362-bp fragment to construct the RNAi plant expression vector.

Figure 1A:
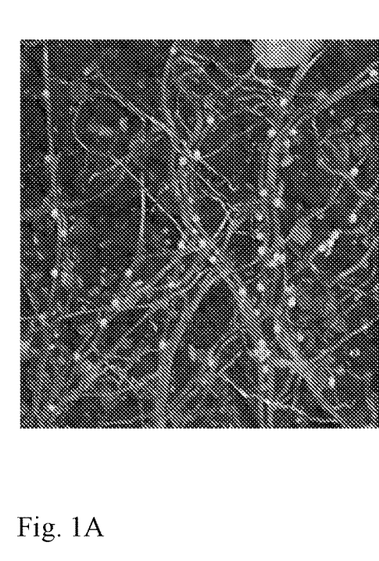
Figure 1B:
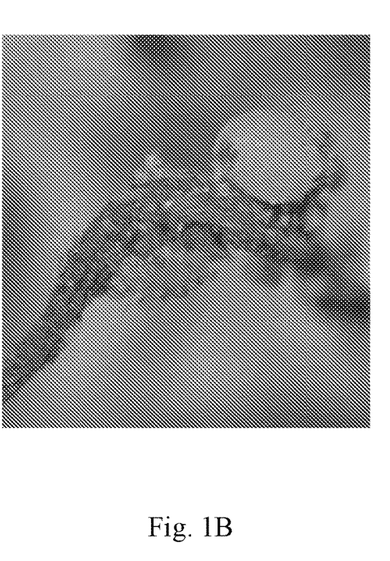
Figure 1C:
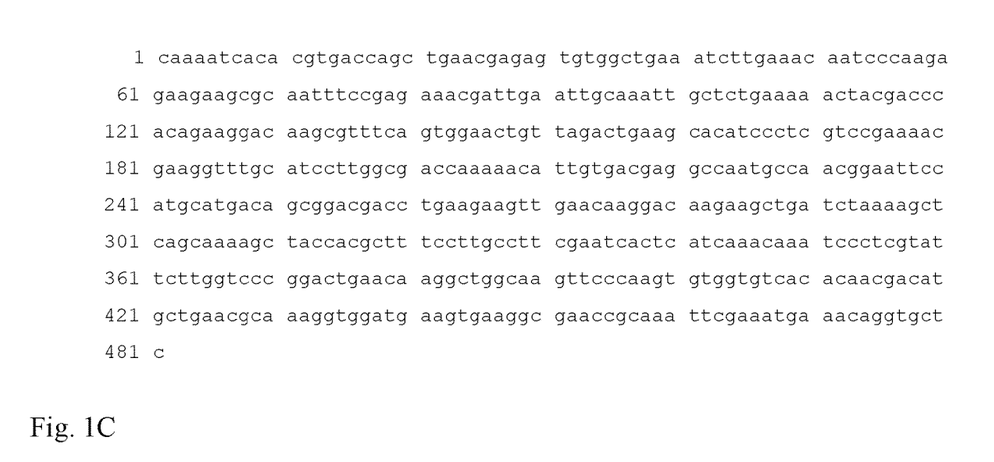
Figure 2A:
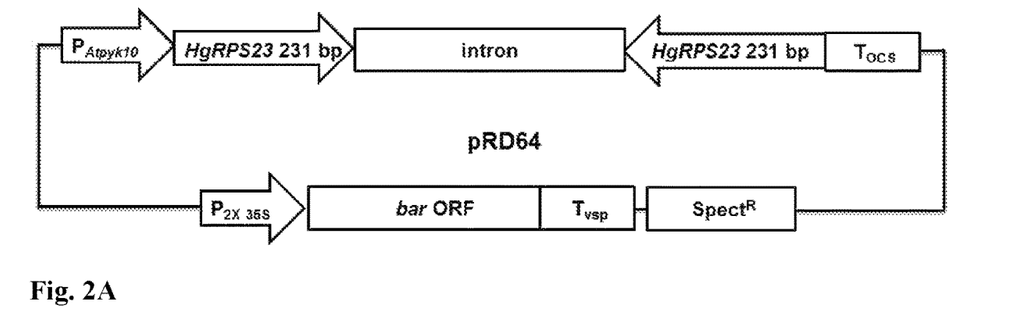
FIGS. 2A and 2B show a schematic diagram of the HgRPS23 siRNA plant transformation vector pRD64 and the sequence of the vector (SEQ ID NO: 2).
Figure 2B:
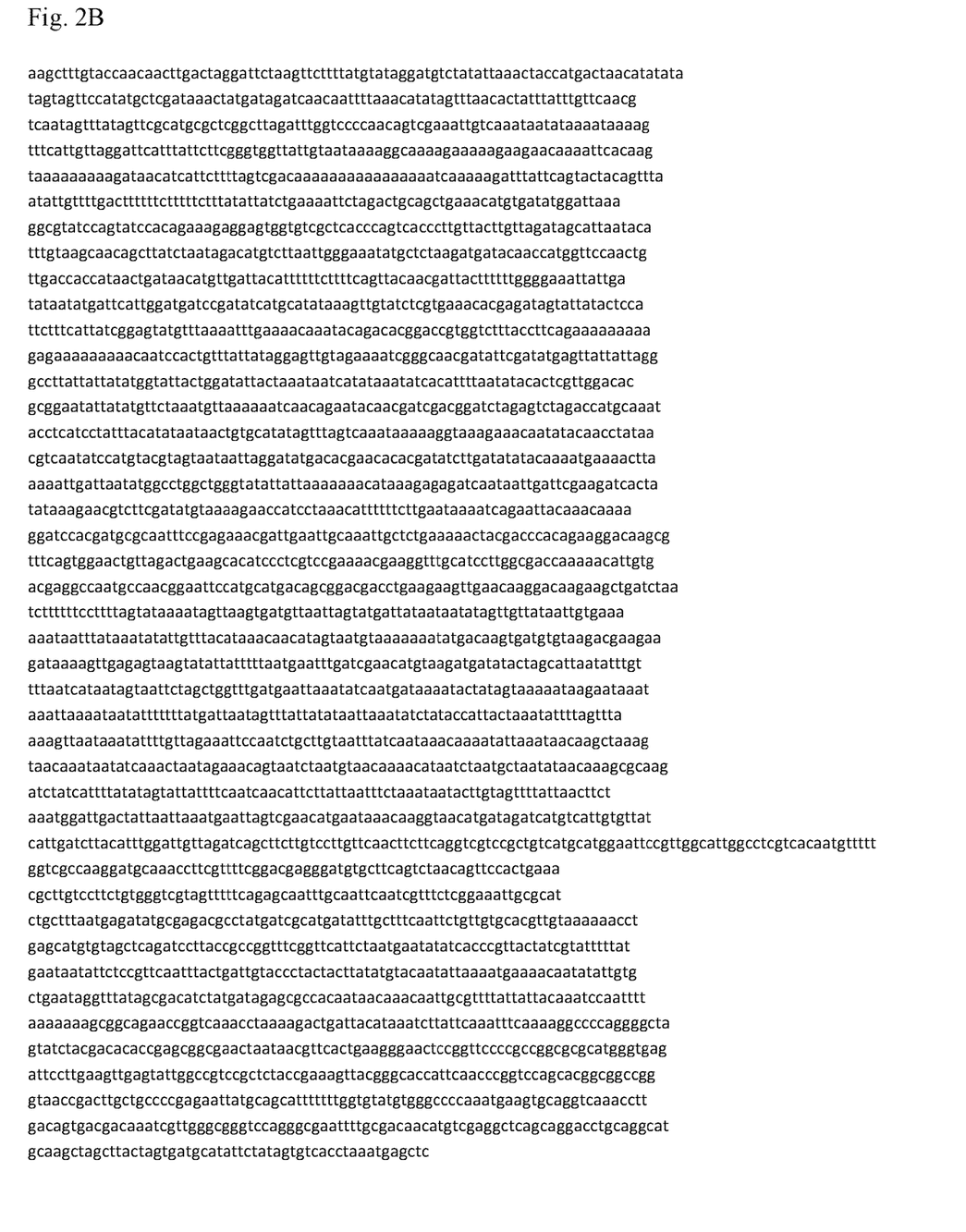

Since SCN attacks the roots of soybean, we decided to express the HgRPS23 siRNAs only in soybean roots. It has been shown that the Arabidopsis pyk10 (myrosinase or thioglucoside glucohydrolase) promoter (Accession No. AJ292756) shows virtually no activities in other parts of the mature plant except in roots (Nitz et al., 2001). Li et al. (2009) (Li et al., 2009) showed that this promoter could drive the expression of Aspergillus ficuum phytase gene in transgenic soybean roots. Therefore, the 1443 bp-fragment of Arabidopsis pyk10 promoter was chosen to drive the HgRPS23 siRNA expression. As shown in FIG. 2A, the 231-bp HgRPS23 sense (S) and anti-sense (AS) sequences are flanked by an intron (742 bp) from the pyruvate orthohphophate dikinase gene as in the siRNA vector pHANNIBAL (Accession No. AJ311872), and terminated by the terminator from the octopine synthase (ocs) gene. The cassette of $P_{Atpyk10}$::HgRPS23-S::intron::HgRPS23-AS::$T_{OCS}$ was synthesized by GenScript (Piscataway, N.J.) and subcloned into pTF101.1 plant expression vector provided by the Plant Transformation Facility, Iowa State University (ISU).

RNA Interference in C. elegans by HgRPS23 siRNAs

Using the online program SIRNA from EMBOSS (http://bioweb.pasteurfr/seqanal/interfaces/sirna.html#outseq) (Yang et al., 2009), the potential siRNA species were predicted from the HgRPS23 231-bp RNAi repeat. The siRNA species (5' AAACUACGACCCACAGAAGGA 3'; SEQ ID NO: 4) with the top score of 9.0 matched to the 5' end of the HgRPS23 231-bp and the 5' end of the C. elegans ribosomal protein large subunit (Accession No. NM_058660).

To test the RNAi effectiveness of our HgRPS23 siRNA, we designed forward and reverse primers with T7 promoter sequence (5' TAATACGACTCACTATAG 3'; (SEQ ID NO: 3) at the 5' ends to amplify the 231 bp-fragment of the HgRPS23 gene by PCR. The dsRNA was produced by T7 RNA polymerase and was used to soak and treat C. elegans (N2 wild type) at L2 stage (Alkharouf et al., 2007). It was observed that after only one day of treatment, the N2 worms treated with the HgRPS23 dsRNA were all dead, evidenced by the non-movement with poking and the straightened phenotype of dead worms that stayed at L2 stage. The control N2 worms treated with only M9 buffer containing 50 mM octopamine were 100% alive and developed into L4 stage. The vitality rate of N2 worms treated with 10 μM cycloheximide, the translation inhibitor, was approximately 20% after one day of soaking. The treated worms were also stained with Sytox Green nucleic acid stain (Molecular Probes, Eugene, Oreg.) to differentiate dead from living worms, confirming the phenotypic observation (data not shown). This experiment was repeated three times, with consistent result that HgRPS23 dsRNA led to 100% lethality in C. elegans through RNAi after one day of soaking.

HgRPS23 siRNAs are Highly Expressed in Transgenic Soybean Roots

The HgRPS23 siRNA plant expression vector pRD64 was provided to the Plant Transformation Facility at ISU. Five different lines of transgenic soybean plants were produced in three independent events via Agrobacterium-mediated transformation of the embryonic axis from mature Williams 82 seeds. The $T_1$ seeds were then tested. Seeds from two lines were not tested due to low seed counts. The other three lines, RU3, RU6B and RU24, were tested for the integration of the bar cassette and the siRNA production by the TaqMan-based RT-qPCR assay.

Figure 3:
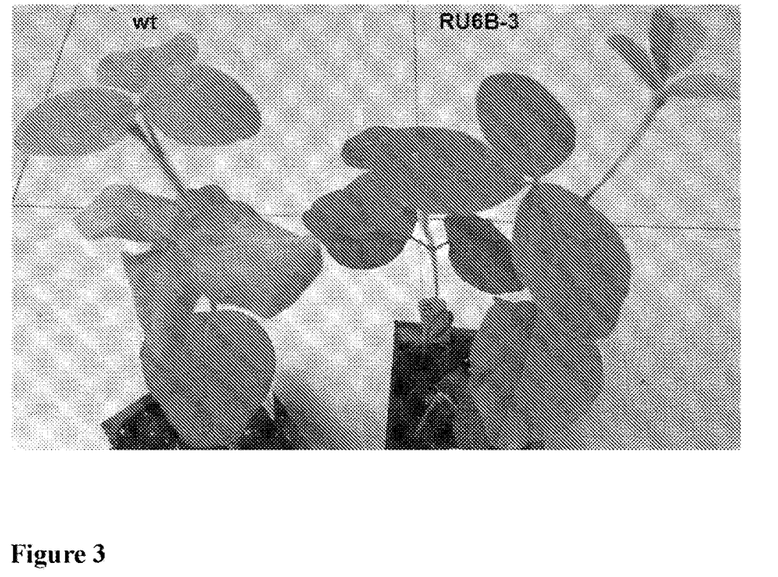
FIG. 3 shows a Herbicide sensitivity test. Untransformed wt displayed yellowing symptom on the painted trifoliate, indicating the sensitivity to glufosinate-ammonium. The trifoliate from transgenic line RU6B-3 remained green.

Two weeks after the germination of transgenic soybean seeds in soil, the first trifoliate leaves were painted with 150 mg/l glufosinate-ammonium with a Q-tip. Three days after the treatment, the herbicide sensitivity of the plants was recorded and transgenic plants were identified. Initially at least 10 $T_1$ seeds from each of RU3, RU6B and RU24 lines were tested. The 10 seeds from each of the $T_2$ plants were later similarly tested for the herbicide sensitivity. A $T_2$ line with all 10 plants resistant to the herbicide was identified as a homozygous line. A representative herbicide sensitivity test result is shown in FIG. 3.

Figure 4:
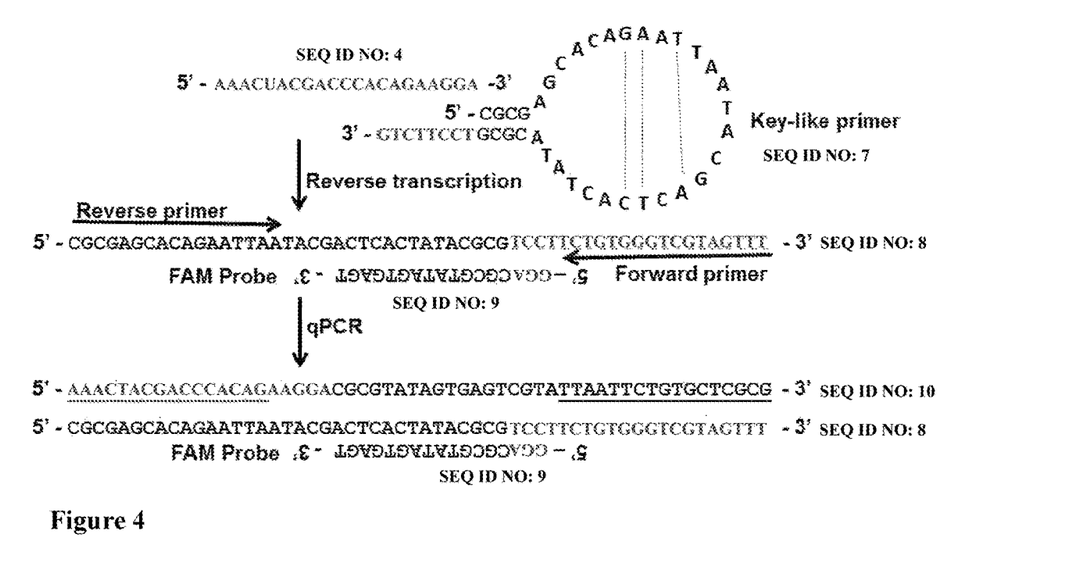

The total RNAs from transgenic soybean plants were isolated and used to conduct the TaqMan RT-qPCR for the expression levels of HgRPS24 siRNA. The key-like oligo was used to carry out the RT reaction (FIG. 4). The RT product was applied to qPCR with the forward, reverse primers and the TaqMan probe (as the TaqMan assay) for the predicted HgRPS23 siRNA species (5' AAACUACGACC-CACAGAAGGA 3', SEQ ID NO: 4). With $2^{-\Delta\Delta Ct}$ analysis using MIR156b as the reference gene (Kulcheski et al,. 2011), our results showed that the $T_1$ lines RU6B-3, RU6B-6, RU6B-8, RU24-7 and RU24-9 had the predicted HgRPS23 siRNA species expressed as high as 20.84-, 10.8-, 9.6-, 12.75- and 12.89-fold, compared to wt soybean roots. Plants from RU3 line showed relatively lower level (2-5-fold) of HgRPS23 siRNA, so it was not used in further testing. The $T_2$ plants RU6B-3-5, RU6B-3-8, RU6B-3-10, RU24-7-4, RU24-9-1 and RU24-9-6 were later shown to express the HgRPS23 siRNA at levels of 18.37-, 21.93-, 20.62-, 15.96-, 16.78- and 15.68-fold by the RT-qPCR assay. The total RNAs isolated from the leaves of transgenic soybean plants were also analyzed by RT-qPCR with the TaqMan probe and the MIR159 as the reference gene. Our results demonstrated that the HgRPS23 levels were negligible in leaves, indicating that the HgRPS23 siRNA were indeed only expressed in the roots of transgenic soybean plants.

HgRPS23 siRNA-Expressing Transgenic Soybean Plants are Resistant to SCN

The $T_1$ and $T_2$ transgenic soybean plants were tested in three batches (RU6B-3, RU24-7, RU24-9, wt; RU6B-6, RU6B-8, wt; RU6B-3-5, RU6B-3-8, RU6B-3-10, RU24-7-4, RU24-9-1, RU24-9-6, wt) for the SCN resistance. Five to ten plants were tested from each line. The number of SCN eggs per gram of root was averaged from two counts from each plant. The final egg number per gram of root was averaged from all the plants in each line and shown in FIG. 5 with the student t-test statistical analysis. Our results showed that all transgenic lines had reduced egg numbers per gram of root. The SCN egg numbers were highly significantly (p<0.01) reduced in $T_1$ lines RU24-9, RU6B-6, RU6B-8, and significantly (p<0.05) in $T_1$ line of RU6B-3. The SCN egg numbers were highly significantly (p<0.01) reduced in all $T_2$ lines (RU6B-3-5, RU6B-3-8, RU6B-3-10, RU24-7-4, RU24-9-1, RU24-9-6) tested. The percentage reduction of egg number ranged from 36.81% (RU24-9-6) to 79.68% (RU24-9) in transgenic lines compared to wt soybean (FIG. 5). The heights of these transgenic soybean plants were also measured and no significant difference was shown compared to wt plants (data not shown). Our data indicate that our HgRPS23 siRNA-expressing transgenic soybean plants were highly resistant to SCN infection.

DISCUSSION

The worldwide presence of SCN and the difficulties of properly managing SCN by the agricultural practices warrant the development of resistant soybeans through the transgenic approach. Transgenic soybean plants over-expressing a soybean salicylic acid (SA) methyltransferase gene, GmSAMT1, has recently been shown to resist multiple races of SCN (Lin et al., 2016). The mechanism of enhanced resistance was attributed to the modulation of expression of genes involved in SA biosynthesis and SA signal transduction in the disease resistance pathways. The transgene was driven by the constitutive CaMV 35S promoter, leading to the over-expression of GmSAMT1 throughout the transgenic soybean plants. Transgenic soybean hairy roots over-expressing the *Arabidopsis* AtNPR1, AtTGA2 and AtPR-5 genes that are involved in plant defense signaling were also shown to produce decreased number of SCN cysts following infection (Matthews et al., 2014). However, transgenic soybean plants were not produced to show the effectiveness of heterologous *Arabidopsis* genes in conferring SCN resistance. The RNAi method taken by Steeves et al. (Steeves et al., 2006) to produce siRNA against the SCN major sperm protein gene seemed to be a better approach compared to the transgene expression to induce SCN resistance, as this RNAi was directly against SCN. However, the expression of siRNA was constitutively driven by the *Arabidopsis* ACT2 promoter, which means the siRNA against the SCN major sperm protein gene was expressed throughout the transgenic soybean plants, although it was only shown that siRNA was detected in the leaf tissues of transgenic soybean plants by Northern blot analysis (Steeves et al., 2006).

To circumvent potential GMO (genetically modified organism) issues, and to better target the pathogenic SCN at the soybean roots, we took the approach of expressing siRNA against the SCN ribosomal protein gene HgRPS23 only in soybean roots with the *Arabidopsis* root-specific pyk10 promoter. Our results showed that the HgRPS23 siRNAs were indeed only expressed in the roots, but not the leaves, of our transgenic soybean plants. The expression level of HgRPS23 siRNA assessed by the TaqMan probe-based RT-qPCR was shown to be 10- to 20-fold higher compared to the untransformed wt plants. The uniquely designed key-like RT primers modeled as previously described (Yang et al., 2009) extended the lengths of siRNAs in the cDNA products after reverse transcription reactions, which made it possible to quantitate the levels of siRNAs by qPCR analysis, negating the utilization of radioactive materials in Northern blot analysis.

The HgRPS23 RNAi has been shown to lead to lethality of SCN J2 worms (Alkharouf et al., 2007). Our bioinformatics analysis indicated that the 5' 225 bp of HgRPS23 shares high homology with the *C. elegans* CeRPL1 at both the nucleic acid and protein levels. The predicted HgRPS23 siRNA (5' AAACUACGACCCACAGAAGGA 3'; SEQ ID NO: 4) shares the exact sequence found in CeRPL1. Our in vitro dsRNA produced from the 225 bp PCR product of HgRPS23 resulted in 100% death rate in *C. elegans* after only one day of soaking and triggering the RNAi pathway in this model nematode. It was reported that the HgRPS23 dsRNA led to partial reduction in the vitality rate in SCN J2 worms after four days of soaking (Alkharouf et al., 2007). Our data suggest that *C. elegans* can serve as an efficient model to test the RNAi for SCN if their genes share homology.

Our SCN infection assay demonstrated that the high expression of HgRPS23 siRNA in the $T_1$ and $T_2$ transgenic soybean roots led to 39-79% reduction in the SCN egg numbers, indicating the effectiveness of this RNAi approach. This approach can be used to express siRNAs in soybean roots against other SCN effectors such as the pectate lyase genes (pel) (Peng et al., 2016), and the genes of HgBioB encoding biotin synthase and HgSLP-1 encoding a bacterial-like protein containing a putative SNARE domain (Bekal et al., 2015). The knocking-down of Hg-pel-6 by RNAi in transgenic soybean hairy roots using CaMV 35S promoter has shown to reduce the invading nematodes and suppress the development of SCN females (Peng et al., 2016), and the HgBioB and HgSLP-1 genes have been shown to be involved in SCN virulence (Bekal et al., 2015). RNAi approach to express siRNAs against these SCN genes specifically in soybean roots should confer SCN resistance in soybean plants.

Furthermore, the recently advanced CRISPR/Cas (clustered regularly interspaced short palindromic repeats/CRISPR-associated)-gene editing technology (Jinek et al., 2012) should be considered to knock-out soybean host factors to interrupt the interaction between soybean plants and *H. glycines*. CRISPR-gene editing has been used to knock-out the rice OsMPK5 gene, which encodes a stress-responsive rice mitogen-activated protein kinase (a negative regulator of rice defense response) (Xie and Yang. 2013). The wheat Mildew-Resistance Locus A1 (TaMLO-A1) has also been mutated by CRISPR-editing (Wang et al., 2014). It was recently shown that RNAi silencing of the putative soybean CLE (CLAVATA3/ENDOSPERM SURROUNDING REGION) receptors resulted in enhanced SCN resistance in transgenic soybean hairy roots (Guo et al., 2015). Employing the precise targeting and easy manipulating platform of CRISPR-gene editing, knocking-out soybean host factors such as the CLE receptors in soybean roots should potentially produce SCN-resistant soybean plants.

REFERENCES

Alkharouf, N. W., Klink, V. P. and Matthews, B. F. (2007) Identification of *Heterodera glycines* (soybean cyst nematode [SCN]) cDNA sequences with high identity to those of *Caenorhabditis elegans* having lethal mutant or RNAi phenotypes. *Exp Parasitol* 115, 247-258.

Bekal, S., Domier, L. L., Gonfa, B., Lakhssassi, N., Meksem, K. and Lambert, K. N. (2015) A SNARE-Like Protein and Biotin Are Implicated in Soybean Cyst Nematode Virulence. *PloS one* 10, e0145601.

Di, R., Purcell, V., Collins, G. B. and Ghabrial, S. A. (1996) Production of transgenic soybean lines expressing the bean pod mottle virus coat protein precursor gene. *Plant cell reports* 15, 746-750.

Duke, S. O. (2015) Perspectives on transgenic, herbicide-resistant crops in the United States almost 20 years after introduction. *Pest management science* 71, 652-657.

Guo, X., Chronis, D., De La Torre, C. M., Smeda, J., Wang, X. and Mitchum, M. G. (2015) Enhanced resistance to soybean cyst nematode *Heterodera glycines* in transgenic soybean by silencing putative CLE receptors. *Plant biotechnology journal* 13, 801-810.

Hamamouch, N., Li, C., Hewezi, T., Baum, T. J., Mitchum, M. G., Hussey, R. S., Vodkin, L. O. and Davis, E. L. (2012) The interaction of the novel 30C02 cyst nematode effector protein with a plant beta-1,3-endoglucanase may suppress host defence to promote parasitism. *Journal of experimental botany* 63, 3683-3695.

Itaya, A., Bundschuh, R., Archual, A. J., Joung, J. G., Fei, Z., Dai, X., Zhao, P. X., Tang, Y., Nelson, R. S. and Ding, B. (2008) Small RNAs in tomato fruit and leaf development. *Biochimica et biophysica acta* 1779, 99-107.

Jinek, M., Chylinski, K., Fonfara, I., Hauer, M., Doudna, J. A. and Charpentier, E. (2012) A programmable dual-RNA-guided DNA endonuclease in adaptive bacterial immunity. *Science* 337, 816-821.

Koenning, S. R. and Wrather, J. A. (2010) Suppressio of soybean yield potential in the continental United States from plant diseases estimated from 2006 to 2009. *Plant Health Prog.*

Kulcheski, F. R., de Oliveira, L. F., Molina, L. G., Almerao, M. P., Rodrigues, F. A., Marcolino, J., Barbosa, J. F., Stolf-Moreira, R., Nepomuceno, A. L., Marcelino-Guimaraes, F. C., Abdelnoor, R. V., Nascimento, L. C., Carazzolle, M. F., Pereira, G. A. and Margis, R. (2011) Identification of novel soybean microRNAs involved in abiotic and biotic stresses. *BMC genomics* 12, 307.

Li, G., Yang, S., Li, M., Qiao, Y. and Wang, J. (2009) Functional analysis of an *Aspergillus ficuum* phytase gene in *Saccharomyces cerevisiae* and its root-specific, secretory expression in transgenic soybean plants. *Biotechnol Lett* 31, 1297-1303.

Lin, J., Mazarei, M., Zhao, N., Hatcher, C. N., Wuddineh, W. A., Rudis, M., Tschaplinski, T. J., Pantalone, V. R., Arelli, P. R., Hewezi, T., Chen, F. and Stewart, C. N., Jr. (2016) Transgenic soybean overexpressing GmSAMT1 exhibits resistance to multiple-HG types of soybean cyst nematode *Heterodera glycines*. *Plant biotechnology journal*.

Lin, J., Mazarei, M., Zhao, N., Zhu, J. J., Zhuang, X., Liu, W., Pantalone, V. R., Arelli, P. R., Stewart, C. N., Jr. and Chen, F. (2013) Overexpression of a soybean salicylic acid methyltransferase gene confers resistance to soybean cyst nematode. *Plant biotechnology journal* 11, 1135-1145.

Matthews, B. F., Beard, H., Brewer, E., Kabir, S., MacDonald, M. H. and Youssef, R. M. (2014) *Arabidopsis* genes, AtNPR1, AtTGA2 and AtPR-5, confer partial resistance to soybean cyst nematode (*Heterodera glycines*) when overexpressed in transgenic soybean roots. *BMC plant biology* 14, 96.

Nitz, I., Berkefeld, H., Puzio, P. S. and Grundler, F. M. (2001) Pyk10, a seedling and root specific gene and promoter from *Arabidopsis thaliana*. *Plant Sci* 161, 337-346.

Pandurangan, S., Pajak, A., Rintoul, T., Beyaert, R., Hernandez-Sebastia, C., Brown, D. C. and Marsolais, F. (2015) Soybean seeds overexpressing asparaginase exhibit reduced nitrogen concentration. *Physiologia plantarum*.

Paz, M. M., Martinez, J. C., Kalvig, A. B., Fonger, T. M. and Wang, K. (2006) Improved cotyledonary node method using an alternative explant derived from mature seed for efficient *Agrobacterium*-mediated soybean transformation. *Plant cell reports* 25, 206-213.

Peng, H., Cui, J., Long, H., Huang, W., Kong, L., Liu, S., He, W., Hu, X. and Peng, D. (2016) Novel pectate lyase genes of *Heterodera glycines* play key roles in the early stage of parasitism. *PloS one* 11, e0149959.

Riggs, R. D. and Schmitt, D. P. (1991) Optimization of the *Heterodera glycines* race test procedure. *J Nematol* 23, 149-154.

Steeves, R. M., CTodd, T. C., Essig, J. S. and Trick, H. N. (2006) Transgenic soybeans expressing siRNAs specific to a major sperm protein gene suppress *Heterodera glycines* reproduction. *Functional Plant Biology* 33, 991-999.

Steeves, R. M., Todd, T. C., SEssig, J. S. and Trick, H. N. (2006) Transgenic soybeans expressing siRNAs specific to a major sperm protein gene suppress *Heterodera glycines* reproduction. *Functional Plant Biology* 33, 991-999.

Wang, Y., Cheng, X., Shan, Q., Zhang, Y., Liu, J., Gao, C. and Qiu, J. L. (2014) Simultaneous editing of three homoeoalleles in hexaploid bread wheat confers heritable resistance to powdery mildew. *Nature biotechnology* 32, 947-951.

Xie, K. and Yang, Y. (2013) RNA-guided genome editing in plants using a CRISPR-Cas system. *Mol Plant* 6, 1975-1983.

Yang, H., Schmuke, J. J., Flagg, L. M., Roberts, J. K., Allen, E. M., Ivashuta, S., Gilbertson, L. A., Armstrong, T. A. and Christian, A. T. (2009) A novel real-time polymerase chain reaction method for high throughput quantification of small regulatory RNAs. *Plant biotechnology journal* 7, 621-630.

Yu, H., Li, Y., Li, X. and Wu, K. (2014) Arthropod abundance and diversity in transgenic Bt soybean. *Environmental entomology* 43, 1124-1134.

Zhou, L., He, H., Liu, R., Han, Q., Shou, H. and Liu, B. (2014) Overexpression of GmAKT2 potassium channel enhances resistance to soybean mosaic virus. *BMC plant biology* 14, 154.

While certain of the preferred embodiments of the present invention have been described and specifically exemplified above, it is not intended that the invention be limited to such embodiments. It will be apparent to one skilled in the art that various changes and modifications can be made therein without departing from the scope of the present invention, as set forth in the following claims.

What is claimed is:

1. A method for modulating soybean cyst nematode infestation in a plant comprising contacting the plant with an effective amount of a composition comprising an RNAi construct which is effective to down modulate expression of Hg-RPS23 in the root of said plant, said down modulation rendering the plant resistant to soybean cyst nematode infestation, wherein said RNAi construct comprising sense and antisense molecules targeting Hg-RPS23 operably linked to an Arabidopsis PyK10 root specific promoter, wherein said RNAi construct is contained within SEQ ID NO: 2.

2. The method of claim 1, wherein the method reduces the number of soybean cyst nematodes in the soil or plant, or on the plant, compared to a plant that has not been contacted with the composition.

3. The method of claim 1, wherein the method promotes growth of the plant, compared to a plant that has not been contacted with the composition.

4. The method of claim 1, wherein the method increases the yield of seeds produced by the plant, compared to a plant that has not been contacted with the composition.

5. An RNAi construct comprising an expression cassette encoding a selectable marker, a root specific promoter operably linked to sense and antisense molecules targeting Hg-RPS23 having SEQ ID NO: 1, said construct being effective to increase resistance to soybean cyst nematode infestation upon expression in a soybean plant, said construct being contained within SEQ ID NO: 2.

6. A soybean plant comprising the RNAi construct of claim 5.

* * * * *

SEQUENCE LISTING

```
<160> NUMBER OF SEQ ID NOS: 10

<210> SEQ ID NO 1
<211> LENGTH: 481
<212> TYPE: DNA
<213> ORGANISM: Heterodera glycines

<400> SEQUENCE: 1
caaaatcaca cgtg

```
gaagaagcgc aatttccgag aaacgattga attgcaaatt gctctgaaaa actacgaccc     120
acagaaggac aagcgtttca gtggaactgt tagactgaag cacatccctc gtccgaaaac     180
gaaggtttgc atccttggcg accaaaaaca ttgtgacgag gccaatgcca acggaattcc     240
atgcatgaca gcggacgacc tgaagaagtt gaacaaggac aagaagctga tctaaaagct     300
cagcaaaagc taccacgctt tccttgcctt cgaatcactc atcaaacaaa tccctcgtat     360
tcttggtccc ggactgaaca aggctggcaa gttcccaagt gtggtgtcac acaacgacat     420
gctgaacgca aaggtggatg aagtgaaggc gaaccgcaaa ttcgaaatga aacaggtgct     480
c                                                                    481

<210> SEQ ID NO 2
<211> LENGTH: 3428
<212> TYPE: DNA
<213> ORGANISM: Artificial Sequence
<220> FEATURE:
<223> OTHER INFORMATION: transformation vector pRD64

<400> SEQUENCE: 2
aagctttgta ccaacaactt gactaggatt ctaagttctt ttatgtatag gatgtctata      60
ttaaactacc atgactaaca tatatatagt agttccatat gctcgataaa ctatgataga    120
tcaacaattt taaacatata gtttaacact atttatttgt tcaacgtcaa tagtttatag    180
ttcgcatgcg ctcggcttag atttggtccc caacagtcga aattgtcaaa taatataaaa    240
taaaagtttc attgttagga ttcatttatt cttcgggtgg ttattgtaat aaaaggcaaa    300
agaaaaagaa gaacaaaatt cacaagtaaa aaaaaagata acatcattct tttagtcgac    360
aaaaaaaaaa aaaaatcaa aaagatttat tcagtactac agtttaatat tgttttgact    420
tttttctttt tctttatatt atctgaaaat tctagactgc agctgaaaca tgtgatatgg    480
attaaaggcg tatccagtat ccacagaaag aggagtggtg tcgctcaccc agtcacccett    540 gttacttgtt agatagcatt aatacatttg taagcaacag cttatctaat agacatgtct    600
taattgggaa atatgctcta agatgataca accatggttc caactgttga ccaccataac    660
tgataacatg ttgattacat ttttttcttttt cagttacaac gattacttt ttggggaaat    720 tattgatata atatgattca ttggatgatc cgatatcatg catataaagt tgtatctcgt    780
gaaacacgag atagtattat actccattct ttcattatcg gagtatgttt aaaatttgaa    840
acaaatacag acacggaccg tggtctttta ccttcagaaa aaaaagaga aaaaaaaca    900 atccactgtt tattataggaa gttgtagaaa tcgggcaac gatattcgat atgagttat    960 attagggcct tattattata tggtattact ggatattact aaataatcat ataaatatca   1020
cattttaata tacactcgtt ggacacgcgg aatattatat gttctaaatg ttaaaaaatc   1080
aacagaatac aacgatcgac ggatctagag tctagaccat gcaaatacct catcctattt   1140
acatataata actgtgcata tagtttagtc aaataaaaag gtaagaaaac aatatacaac   1200
ctataacgtc aatatccatg tacgtagtaa taattaggat atgacacgaa cacacgatat   1260
cttgatatat acaaaatgaa aacttaaaaa ttgattaata tggcctggct gggtatatta   1320
ttaaaaaaac ataagagag atcaataatt gattcgaaga tcactatata agaacgtct   1380 tcgatatgta aagaaccat cctaaacatt ttttcttgaa taaaatcaga attacaaaca   1440
aaaggatcca cgatgcgcaa tttccgagaa acgattgaat tgcaaattgc tctgaaaac   1500 tacgacccac agaaggacaa gcgtttcagt ggaactgtta gactgaagca catccctcgt   1560
```

```
ccgaaaacga aggtttgcat ccttggcgac caaaaacatt gtgacgaggc caatgccaac    1620
ggaattccat gcatgacagc ggacgacctg aagaagttga acaaggacaa gaagctgatc    1680
taatcttttt tccttttagt ataaaatagt taagtgatgt taattagtat gattataata    1740
atatagttgt tataattgtg aaaaaataat ttataaatat attgtttaca taaacaacat    1800
agtaatgtaa aaaaatatga caagtgatgt gtaagacgaa gaagataaaa gttgagagta    1860
agtatattat ttttaatgaa tttgatcgaa catgtaagat gatatactag cattaatatt    1920
tgttttaatc ataatagtaa ttctagctgg tttgatgaat taaatatcaa tgataaaata    1980
ctatagtaaa aataagaata aataaattaa aataatattt ttttatgatt aatagtttat    2040
tatataatta aatatctata ccattactaa atattttagt ttaaaagtta ataaatattt    2100
tgttagaaat tccaatctgc ttgtaattta tcaataaaca aaatattaaa taacaagcta    2160
aagtaacaaa taatatcaaa ctaatagaaa cagtaatcta atgtaacaaa acataatcta    2220
atgctaatat aacaaagcgc aagatctatc attttatata gtattatttt caatcaacat    2280
tcttattaat ttctaaataa tacttgtagt tttattaact tctaaatgga ttgactatta    2340
attaaatgaa ttagtcgaac atgaataaac aaggtaacat gatagatcat gtcattgtgt    2400
tatcattgat cttacatttg gattgttaga tcagcttctt gtccttgttc aacttcttca    2460
ggtcgtccgc tgtcatgcat ggaattccgt tggcattggc ctcgtcacaa tgttttggt    2520 cgccaaggat gcaaaccttc gttttcggac gagggatgtg cttcagtcta acagttccac    2580
tgaaacgctt gtccttctgt gggtcgtagt ttttcagagc aatttgcaat tcaatcgttt    2640
ctcggaaatt gcgcatctgc tttaatgaga tatgcgagac gcctatgatc gcatgatatt    2700
tgctttcaat tctgttgtgc acgttgtaaa aaacctgagc atgtgtagct cagatcctta    2760
ccgccggttt cggttcattc taatgaatat atcacccgtt actatcgtat ttttatgaat    2820
aatattctcc gttcaattta ctgattgtac cctactactt atatgtacaa tattaaaatg    2880
aaaacaatat attgtgctga ataggtttat agcgacatct atgatagagc gccacaataa    2940
caaacaattg cgttttatta ttacaaatcc aattttaaaa aaagcggcag aaccggtcaa    3000
acctaaaaga ctgattacat aaatcttatt caaatttcaa aaggcccag gggctagtat    3060 ctacgacaca ccgagcggcg aactaataac gttcactgaa gggaactccg gttccccgcc    3120
ggcgcgcatg ggtgagattc cttgaagttg agtattggcc gtccgctcta ccgaaagtta    3180
cgggcaccat tcaacccggt ccagcacggc ggccgggtaa ccgacttgct gccccgagaa    3240
ttatgcagca tttttttggt gtatgtgggc cccaaatgaa gtgcaggtca aaccttgaca    3300
gtgacgacaa atcgttgggc gggtccaggg cgaattttgc gacaacatgt cgaggctcag    3360
caggacctgc aggcatgcaa gctagcttac tagtgatgca tattctatag tgtcacctaa    3420
atgagctc                                                            3428
```

<210> SEQ ID NO 3
<211> LENGTH: 18
<212> TYPE: DNA
<213> ORGANISM: Artificial Sequence
<220> FEATURE:
<223> OTHER INFORMATION: T7 promoter sequence

<400> SEQUENCE: 3
taatacgact cactatag                                                 18

<210> SEQ ID NO 4
<211> LENGTH: 21

```
<212> TYPE: RNA
<213> ORGANISM: Artificial Sequence
<220> FEATURE:
<223> OTHER INFORMATION: siRNA

<400> SEQUENCE: 4
aaacuacgac ccacagaagg a                                              21

<210> SEQ ID NO 5
<211> LENGTH: 21
<212> TYPE: RNA
<213> ORGANISM: Artificial Sequence
<220> FEATURE:
<223> OTHER INFORMATION: MIR156b

<400> SEQUENCE: 5
ugacagaaga gagagagcac a                                              21

<210> SEQ ID NO 6
<211> LENGTH: 21
<212> TYPE: RNA
<213> ORGANISM: Artificial Sequence
<220> FEATURE:
<223> OTHER INFORMATION: MIR159

<400> SEQUENCE: 6
uuuggauuga agggagcucu a                                              21

<210> SEQ ID NO 7
<211> LENGTH: 43
<212> TYPE: DNA
<213> ORGANISM: Artificial Sequence
<220> FEATURE:
<223> OTHER INFORMATION: Key-like primer

<400> SEQUENCE: 7
cgcgagcaca gaattaatac gactcactat acgcgtcctt ctg                      43

<210> SEQ ID NO 8
<211> LENGTH: 56
<212> TYPE: DNA
<213> ORGANISM: Artificial Sequence
<220> FEATURE:
<223> OTHER INFORMATION: Synthetic sequence

<400> SEQUENCE: 8
cgcgagcaca gaattaatac gactcactat acgcgtcctt ctgtgggtcg tagttt        56

<210> SEQ ID NO 9
<211> LENGTH: 17
<212> TYPE: DNA
<213> ORGANISM: Artificial Sequence
<220> FEATURE:
<223> OTHER INFORMATION: FAM probe

<400> SEQUENCE: 9
ggacgcgtat agtgagt                                                   17

<210> SEQ ID NO 10
<211> LENGTH: 56
```

```
<212> TYPE: DNA
<213> ORGANISM: Artificial Sequence
<220> FEATURE:
<223> OTHER INFORMATION: Synthetic Sequence

<400> SEQUENCE: 10
aaactacgac ccacagaagg acgcgtatag tgagtcgtat taattctgtg ctcgcg        56
```